United States Patent [19]

Wood et al.

[11] Patent Number: 4,642,302

[45] Date of Patent: Feb. 10, 1987

[54] CATALYSTS HAVING ALKOXIDE-MODIFIED SUPPORTS AND METHOD OF INCREASING THE CATALYTIC ACTIVITY OF A CATALYTIC METAL

[75] Inventors: Clayton D. Wood, Framingham; Philip E. Garrou, Holliston; Iwao Kohatsu, Lexington, all of Mass.; Edward F. Gleason, Berkeley, Calif.

[73] Assignee: The Dow Chemical Company, Midland, Mich.

[21] Appl. No.: 809,543

[22] Filed: Dec. 16, 1985

Related U.S. Application Data

[62] Division of Ser. No. 655,991, Sep. 28, 1984, Pat. No. 4,559,364, which is a division of Ser. No. 567,112, Dec. 30, 1983, abandoned.

[51] Int. Cl.$^4$ .................... B01J 21/04; B01J 21/06; B01J 21/08; B01J 23/64

[52] U.S. Cl. .................... 502/332; 502/242; 502/246; 502/258; 502/259; 502/260; 502/261; 502/262; 502/325; 502/333; 502/334; 502/335; 502/336

[58] Field of Search .............. 502/242, 246, 258, 259, 502/260, 261, 325, 332, 333, 334, 335, 336, 262

[56] References Cited

U.S. PATENT DOCUMENTS

| | | | |
|---|---|---|---|
| 3,873,469 | 3/1975 | Foster et al. | 423/213.5 X |
| 4,076,792 | 2/1978 | Foster et al. | 502/334 |
| 4,171,320 | 10/1979 | Vannice et al. | 518/715 |
| 4,269,737 | 5/1981 | Grenoble et al. | 502/204 |
| 4,376,721 | 3/1983 | Huang | 502/171 |

Primary Examiner—W. J. Shine

[57] ABSTRACT

A catalyst composition comprising a catalytic metal and a support, the support being prepared by depositing a metal alkoxide on a core support, then calcining the support.

16 Claims, No Drawings

CATALYSTS HAVING ALKOXIDE-MODIFIED SUPPORTS AND METHOD OF INCREASING THE CATALYTIC ACTIVITY OF A CATALYTIC METAL

CROSS-REFERENCE TO RELATED APPLICATION

This is a divisional of Application Ser. No. 655,991, filed Sept. 28, 1984, now U.S. Pat. No. 4,559,364, which was a divisional of Application Ser. No. 567,112, filed Dec. 30, 1983, now abandoned.

BACKGROUND OF THE INVENTION

The present invention relates to supported metal catalysts.

Catalytic metals play an important role in heterogeneous catalysis. The catalytic metals typically are employed on various support materials, as only the surface of a metal particle can participate in a catalytic process. Many people have proposed various solutions to the long-standing problem of how to disperse catalytic metals more efficiently on the surface of a support material. However, the art has not recognized the present invention as being an improved solution to the problem.

SUMMARY OF THE INVENTION

In one aspect, the present invention is an improved catalyst composition comprising a catalytic metal on an alkoxide-modified support.

In another aspect, the invention is a method of increasing the catalytic activity of a catalytic metal, the method comprising supporting the catalytic metal on a support prepared by contacting a metal alkoxide with a core support, then calcining the mixture of the metal alkoxide and the core support thereby leaving a coating on the core support, the coating comprising the metal oxide derived from the calcination of the metal alkoxide.

In yet another aspect, the present invention is the use of a catalyst composition of the present invention in a process for producing methane in an improved yield by contacting carbon monoxide and hydrogen under reaction conditions.

Surprisingly, the supported catalyst composition of the present invention exhibits increased catalytic activity compared to supports not treated by the method of this invention. Thus, the catalyst composition of the present invention is useful in and catalytic process in which enhanced activity of a supported metal catalyst is desirable. For example, the proper catalyst composition can be employed in the production of methane in improved yields.

DETAILED DESCRIPTION OF THE INVENTION

The catalyst composition of the present invention has two required components: a catalytic metal; and an alkoxide-modified support. For the purposes of the present invention, the term "alkoxide-modified support" means a material prepared by depositing a thin layer of a metal alkoxide on a core support material and then converting the metal alkoxide to the oxide of said metal.

The alkoxide-modified support comprises a core support material having on its outer surface a thin layer of a metal oxide produced from a precursor metal alkoxide. The core support material can be any material, such as a refractory oxide, which will not decompose or melt when subjected to calcination. Examples of typical core support materials include alumina, zirconia, boria, thoria, magnesia, titania, tantala, chromia, silica, kieselguhr and mixtures of these materials. The aluminas and silicas are preferred in view of their low cost. The core support material typically has a surface area in the region of about 0.10 to 500 m$^2$/g, preferably 20 to 200 m$^2$/g, and most preferably over 100 m$^2$/g prior to the deposition of the metal alkoxide precursor. These surface areas are as measured by the Brunauer-Emmett-Teller (BET) method. The BET method is described by R. B. Anderson, *Experimental Methods in Catalytic Research*, pp. 48–66, Academic Press, 1968.

The precursor metal alkoxide can be the alkoxide of almost any metal so long as said metal alkoxide will thermally decompose to form a metal oxide. Examples of preferred metals for use in the precursor metal alkoxide include the metals of Groups IIIA, IVA, IVB and VB of the periodic table of the elements. Examples of typical precursor metal alkoxides include Al(OCH(CH$_2$CH$_3$)(CH$_3$))$_3$, Ti(OCH(CH$_3$)$_2$)$_4$, Ta(OCH(CH$_3$)$_2$)$_5$, Si(OC$_2$H$_5$)$_4$, Nb$_2$(OC$_2$H$_5$)$_{10}$, Ta$_2$(OC$_2$H$_5$)$_{10}$, and the like. Typically, the alkoxide moiety has from 1 to about 10 carbon atoms, preferably from about 2 to about 4 carbon atoms.

The alkoxide-modified support is prepared by techniques known in the art, e.g., incipient wetness impregnation techniques, etc. Metal oxide precursors are deposited on the selected core support material followed by conversion into the oxide form by calcination. The alkoxide-modified support is prepared by impregnating the desired core support material with a solution of an alkoxide precursor of the desired metal oxide. The solution used in impregnating the core support material may be aqueous or organic, the only requirement being that an adequate amount of precursor compound for the selected metal oxide is soluble in the solvent used in preparing the impregnating solution. Aqueous or alcohol solutions, preferably aqueous or ethanol solutions, are normally used for convenience. When using the impregnaton technique the metal alkoxide impregnating solution is contacted with the core support material for a time sufficient to deposit the metal alkoxide precursor material onto the carrier either by selective adsorption or, alternatively, the excess solvent may be evaporated during drying leaving behind the precursor metal alkoxide salt. Advantageously, the incipient wetness technique may be used whereby just enough of a precursor metal alkoxide solution is added to dampen and fill the pores of the powder of the above-recited core support material.

The composite thus prepared by any of the above-recited techniques, or by any other technique known in the art, is dried at a temperature of from 50° to 300° C. to remove the excess solvent and then converted into the oxide form by exposure at temperatures of from 150° to 800° C., preferably 300°–700° C. in an atmosphere such as O$_2$, air, He, Ar or combinations thereof. This exposure is for a time sufficient to convert essentially all of the metal alkoxide precursor into metal oxide. The calcination is useful to decompose the metal precursor to the oxide form. Calcination, however, may not be required for certain metal precursors which readily convert into metal oxides.

The catalytic metal can be any metal or metal compound having catalytic activity. Typical catalytic metals include the transition metals. Examples of preferred catalytic metals include the metals of Group VIII of the periodic table of the elements, i.e., iron, ruthenium, osmium, cobalt, rhodium, iridium, nickel, palladium and platinum. The catalytic metal is deposited on the alkoxide-modified support via methods known in the art such as, for example, impregnation of the alkoxide-modified support with a salt of the catalytic metal. The salt of the catalytic metal is converted to the metal by exposing the salt to a reducing atmosphere via methods known in the art. It is preferred to reduce the salt of the catalytic metal in situ, i.e., while the salt is in the reaction vessel.

Typically, the precursor metal alkoxide is employed in an amount sufficient to result in a finished alkoxide-modified support which has, after calcination, at least a molecular monolayer of the metal oxide, formed from the metal alkoxide, covering the entire outer surface of the core support material. Typically, the catalytic metal is employed in a catalytic amount. Preferably, the finished catalyst of the present invention will have a composition as follows: from about 0.1 to about 10 weight percent catalytic metal; from about 0.1 to about 30 weight percent of metal oxide from alkoxide precursor; and the remainder being core support material. More preferably, the finished catalyst of the present invention will have a composition as follows: from about 0.5 to about 5 weight percent catalytic metal; from about 1 to about 5 weight percent metal oxide from alkoxide precursor; and the remainder being core support material.

The catalyst composition of the present invention is useful in any application in which enhanced activity of a supported catalytic metal is desirable. The production of methane from CO and $H_2$ is an example of a preferred use of the catalyst composition of the present invention. The art contains many examples of metals known to be useful in reacting carbon monoxide with hydrogen to produce a variety of compounds, including hydrocarbons and oxygenated compounds. These metals include, among others, Mo, W, Rh, Ru, Re, Pd, Ni, Co, and Fe. In what has come to be called the Fischer-Tropsch Synthesis, carbon monoxide and hydrogen are reacted over a metal catalyst to produce saturated and unsaturated hydrocarbons and oxygenated compounds containing from 1 to as many as 1000 carbon atoms. The hydrocarbons can be aliphatic, alicyclic, or aromatic. Commercial utilization of this synthesis prior to 1950 was accomplished largely in Germany and is summarized in Storch, Columbic, and Anderson: *The Fischer-Tropsch and Related Synthesis*, John Wiley and Sons, New York 1951.

The major disadvantage in the prior art processes and catalysts is that most of them are not capable of selectively producing methane. Surprisingly, at least one catalyst of the present invention may be used to produce methane selectively by contacting carbon monoxide and hydrogen in the presence of said catalyst under reaction conditions.

The carbon monoxide required for the process can be obtained from any carbon source, such as from the degradation of coal. The molar ratio of hydrogen to carbon monoxide ranges generally from at least about 0.1 to about 10, and preferably is from about 1 to about 3.

Process reaction conditions can vary over a rather wide range. The pressure can vary from at least about 1 psig up to about 1500 psig. Atmospheric pressure is preferred for convenience. The reaction temperature typically ranges from at least about 200° C. to about 600° C. and preferably is from about 200° C. to about 300° C.

Ruthenium is the preferred catalytic metal for use in the production of methane via the process of the present invention.

The following examples and comparative experiments are given to illustrate the invention and should not be construed as limiting its scope. All parts and percentages are by weight unless otherwise indicated.

SPECIFIC EMBODIMENTS

Preparation of Alkoxide-Modified Supports

Preparation 1

A solution 4.5 g of $Al(OCH(CH_2CH_3)(CH_3))_3$, obtained from Alfa Products, a Division of Morton Thiokol, Inc., in 20 ml of hexanes is added to a suspension of 10 g of $\gamma$-$Al_2O_3$ core support material, obtained from Strem Chemicals, Inc., and having a BET surface area of 100 $m^2$/g in 125 ml of hexanes to form a mixture. The mixture is stirred for 2 hours at room temperature under an inert atmosphere. Then the hexanes are removed under vacuum to yield a white powder. The powder is calcined in air at 450° C. for 15 hours to form an $AlO_x$/$\gamma$-$Al_2O_3$ alkoxide-modified support having a BET surface area of 120 $m^2$/g. The weight ratio of $AlO_x$ to $\gamma$-aluminum is approximately 0.05.

Preparation 2

The procedure of Preparation 1 is followed except that the precursor metal alkoxide is $Ti(OCH(CH_3)_2)_4$, and the final product alkoxide-modified support is $TiO_x$/$\gamma$-$Al_2O_3$.

Preparation 3

The procedure of Preparation 1 is repeated except that the precursor metal alkoxide is $Ta(OCH(CH_3)_2)_4$, and the alkoxide-modified support is $TaO_x$ on $\gamma$-$Al_2O_3$.

Example 1

Catalyst Preparation

Five grams of the support of Preparation 1 are added to a 100 ml solution of 0.64 g of $RuCl_3.(1-3H_2O)$ in $H_2O$. The mixture is stirred for an hour and the water is removed under vacuum with steam heat. The solids are dried overnight at 110° C. in air. Analysis indicates that the solids contain 5 weight percent Ru.

General Reaction Procedure

A 16-inch long piece of 9/16 inch tubing of type 316 stainless steel is employed vertically as a reactor. The reactor is equipped with a means for temperature control, and has 1 g of catalyst held in place by quartz wool in the center of the reactor. The catalyst is reduced in situ at 400° C. for 15 hours with hydrogen at 50 cc/min. Then the reactor is cooled to 300° C. in flowing hydrogen gas. Then a feed stream consisting of 2 moles hydrogen per mole of CO is fed to the reactor under a pressure of 1 atmosphere (14.7 psig) at 100 cc/min (gas hourly space velocity=6000/hr). The product stream is analyzed using gas chromatographic methods capable of detecting $C_1$-$C_5$ hydrocarbons, $C_1$-$C_5$ alcohols, $H_2$, CO, and $CO_2$.

Examples 2-5 and Comparative Experiments 1-4

The General Reaction Procedure is followed for each Example and Comparative Experiment, and each run is conducted for a 24-hour period. The results of each run are summarized in Table I.

Example 2

The catalyst of Example 1 is employed.

Comparative Experiment 1

The catalyst is 5 weight percent Ru on the $\gamma$-$Al_2O_3$ core support material of Preparation 1 with no alkoxide modification.

Example 3

The catalyst is 5 weight percent Ru on the support of Preparation 2.

Comparative Experiment 2

The catalyst is 5 weight percent Ru on $TiO_2$, the untreated $TiO_2$ having a BET surface area of 100 $m^2/g$.

Example 4

The catalyst is 5 weight percent Ru on the support of Preparation 3.

Comparative Experiment 3

The catalyst is 5 weight percent Ru on $Ta_2O_5$, the untreated $Ta_2O_5$ having a BET surface area of 5 $m^2/g$.

TABLE I

| Methanation Results with 5 Weight Percent Ruthenium Catalysts | | | |
|---|---|---|---|
| Run | Catalyst | Conversion of CO (mole %) | Selectivity to Methane (mole %) |
| Ex. 2 | Ru/$AlO_x$/$\gamma$—$Al_2O_3$ | 99 | 100 |
| C.E. 1 | Ru/$\gamma$—$Al_2O_3$ | 62 | 99 |
| Ex. 3 | Ru/$TiO_x$/$\gamma$—$Al_2O_3$ | 98 | 100 |
| C.E. 2 | Ru/$TiO_2$ | 58 | 100 |
| Ex. 4 | Ru/$TaO_x$/$\gamma$—$Al_2O_3$ | 97 | 100 |
| C.E. 3 | Ru/$Ta_2O_5$ | 17 | 37 |

The results summarized in Table I indicate that the catalyst of the present invention unexpectedly and significantly outperforms, under identical conditions, conventional catalysts supported on materials used as the core support material of the catalyst of the present invention.

Example 5 and Comparative Experiment 4

Example 2 and Comparative Experiment 1 are repeated except that the catalyst has 1 weight percent ruthenium. The results are summarized in Table II.

TABLE II

| Methanation with 1 Weight Percent Ruthenium Catalyst | | | |
|---|---|---|---|
| Run | Catalyst | Conversion of CO (mole %) | Selectivity to $CH_4$ (mole %) |
| Ex. 5 | Ru/$AlO_x$/$\gamma$—$Al_2O_3$ | 90 | 99 |
| C.E. 4 | Ru/$\gamma$—$Al_2O_3$ | 3 | 81 |

Surprisingly, at the lower catalyst loading, 1 weight percent ruthenium, the catalyst of the present invention significantly outperforms the equivalent catalytic metal on the conventional support. More surprisingly, a loading of 1 weight percent ruthenium on an alkoxide modified support outperforms a conventional catalyst having a loading of 5 weight percent ruthenium (see Comparative Experiment 1).

As previously mentioned, the preceding examples serve only to illustrate the invention and its advantages, and they should not be interpreted as limiting since further modifications of the disclosed invention will be apparent to those skilled in the art. All such modifications are deemed to be within the scope of the invention as defined by the following claims.

What is claimed is:

1. A catalyst composition comprising a catalytic metal and an alkoxide-modified support, which support comprises a core support material having (a) a surface area of from about 20 to 200 $m^2/gram$; and having (b) on the outer surface thereof a metal oxide produced from a precursor metal alkoxide.

2. The composition of claim 1 wherein the catalytic metal is a Group VIII metal.

3. The composition of claim 1 wherein the core support is a metal oxide.

4. The composition of claim 1 wherein the alkoxide anion of the metal alkoxide has from 1 to about 10 carbon atoms.

5. A catalyst composition consisting essentially of the composition of claim 1.

6. The composition of claim 1 wherein the catalytic metal is from about 0.1 to about 10 weight percent of the total composition.

7. The composition of claim 6 wherein the metal oxide layer prepared from the metal alkoxide is from about 0.1 to about 30 weight percent of the total composition.

8. The composition of claim 7 wherein the core support material is silica or alumina, the catalytic metal is from about 0.5 to about 5 weight percent of the composition, and the metal oxide from metal alkoxide is from about 1 to about 5 weight percent of the composition.

9. The composition of claim 1 wherein the metal of the metal alkoxide is a metal of Group IIIA, IVA, IVB or VB.

10. The composition of claim 1 wherein the alkoxide anion of the metal alkoxide has from about 2 to about 4 carbon atoms.

11. The composition of claim 1 wherein the metal of the metal alkoxide is aluminum, tantalum, or titanium and the catalytic metal is ruthenium.

12. A method of increasing the catalytic activity of a catalytic metal, the method comprising supporting the catalytic metal on a support prepared by contacting a metal alkoxide with a core support, which support has a surface area of from about 20 to about 200 $m^2/g$, then treating the mixture of the metal alkoxide and the core support to remove the carbon atoms therefrom, thereby leaving a coating on the core support, the coating comprising the metal oxide from the metal alkoxide.

13. The method of claim 12 wherein the treating step to remove the carbon atoms is a step comprising calcination.

14. The method of claim 12 wherein the core support is an oxide of a metal of Group IIIA, IVA, IVB or VB.

15. The method of claim 12 wherein the metal of the metal alkoxide is a metal of Group IIIA, IVA, IVB or VB.

16. The method of claim 12 wherein the catalytic metal is a metal of Group VIII.

* * * * *